(12) United States Patent
Danley et al.

(10) Patent No.: US 8,821,008 B2
(45) Date of Patent: Sep. 2, 2014

(54) SIMULTANEOUS DIFFERENTIAL THERMAL ANALYSIS SYSTEM

(75) Inventors: Robert L. Danley, Collingswood, NJ (US); Xiaoping Hu, New Castle, DE (US)

(73) Assignee: Waters Technologies Corporation, Milford, MA (US)

( * ) Notice: Subject to any disclaimer, the term of this patent is extended or adjusted under 35 U.S.C. 154(b) by 936 days.

(21) Appl. No.: 12/766,964

(22) Filed: Apr. 26, 2010

(65) Prior Publication Data

US 2010/0278209 A1 Nov. 4, 2010

Related U.S. Application Data

(60) Provisional application No. 61/173,764, filed on Apr. 29, 2009.

(51) Int. Cl.
| | |
|---|---|
| *G01N 25/00* | (2006.01) |
| *G01G 21/07* | (2006.01) |
| *G01N 5/04* | (2006.01) |
| *G01G 21/22* | (2006.01) |
| *G01G 21/16* | (2006.01) |
| *G01G 21/23* | (2006.01) |

(52) U.S. Cl.
CPC ............ *G01G 21/07* (2013.01); *G01N 5/04* (2013.01); *G01G 21/22* (2013.01); *G01G 21/16* (2013.01); *G01G 21/23* (2013.01)
USPC .................. 374/10; 374/12; 374/14

(58) Field of Classification Search
CPC ............................ G01G 7/02; G01G 21/244
USPC .............. 374/100, 163, 203, 208, 10–14, 45; 177/212.21, 201, 229; 73/862.31, 73/862.634, 862.635
See application file for complete search history.

(56) References Cited

U.S. PATENT DOCUMENTS

| | | | | |
|---|---|---|---|---|
| 3,519,095 | A | * | 7/1970 | Tomes ...................... 177/210 R |
| 3,685,604 | A | | 8/1972 | Smith et al. |
| 4,099,587 | A | * | 7/1978 | Kaufmann ............. 177/210 EM |
| 4,331,035 | A | * | 5/1982 | Eisele et al. .................... 73/765 |
| 4,553,618 | A | * | 11/1985 | Kusmenskji et al. ......... 177/185 |
| 5,270,497 | A | * | 12/1993 | Komoto ........................ 177/212 |
| 5,321,719 | A | * | 6/1994 | Reed et al. ....................... 374/14 |

(Continued)

FOREIGN PATENT DOCUMENTS

| | | |
|---|---|---|
| EP | 1925920 | 5/2008 |
| JP | 08129015 | 5/2008 |
| WO | 2008145426 | 12/2008 |

OTHER PUBLICATIONS

PCT/ISA/210, WO, Aug. 4, 2010, ISR for PCT/US10/032669.

(Continued)

*Primary Examiner* — R. A. Smith
*Assistant Examiner* — Tania Courson
(74) *Attorney, Agent, or Firm* — Waters Technologies Corporation

(57) ABSTRACT

A balance for a simultaneous differential thermal analysis instrument that combines gravimetric measurements with measurements that require propagation of electrical signals from the sample holder to an apparatus for recording the electrical signals. In one embodiment of the invention, conductive flat planar strip flexure pivots are used in a single-meter movement balance to mechanically and electrically couple the components of the balance mechanism to the apparatus that records the electrical signals.

28 Claims, 7 Drawing Sheets

(56) References Cited

U.S. PATENT DOCUMENTS

| | | | |
|---|---|---|---|
| 5,347,092 A * | 9/1994 | Buchs et al. | 177/212 |
| 5,826,983 A | 10/1998 | Nakamura et al. | |
| 6,057,516 A | 5/2000 | Nakamura et al. | |
| 6,232,567 B1 | 5/2001 | Bonino et al. | |
| 6,958,453 B2 * | 10/2005 | Burkhard | 177/184 |
| 7,306,365 B2 * | 12/2007 | Danley | 374/10 |
| 7,416,328 B2 * | 8/2008 | Danley et al. | 374/14 |
| 7,429,705 B2 * | 9/2008 | Genoud et al. | 177/210 EM |
| 7,566,167 B2 * | 7/2009 | Danley et al. | 374/14 |
| 7,619,170 B2 | 11/2009 | Burkhard et al. | |
| 7,851,713 B2 * | 12/2010 | Burkhard et al. | 177/210 EM |
| 7,922,386 B2 * | 4/2011 | Tanaka | 374/14 |
| 8,042,992 B2 * | 10/2011 | Wijffels | 374/12 |
| 2006/0201719 A1 * | 9/2006 | Burkhard | 177/212 |
| 2006/0266562 A1 * | 11/2006 | Genoud et al. | 177/212 |
| 2008/0121048 A1 | 5/2008 | Burkhard et al. | |
| 2008/0144694 A1 | 6/2008 | Danley et al. | |
| 2010/0278210 A1 * | 11/2010 | Danley et al. | 374/14 |
| 2013/0208759 A1 * | 8/2013 | Danley et al. | 374/10 |

OTHER PUBLICATIONS

PCT/ISA/237, WO, Aug. 4, 2010, Written Opinion for PCT/US10/032669.
PCT International Search Report for PCT/US10/32673, filed Apr. 28, 2010, 4 pages.
PCT International Written Opinion Report for PCT/US10/32673, filed Apr. 28, 2010, 6 pages.
Translation of Notice of Rejection for Japanese Patent Application No. 2012-508618, mailing date of Feb. 10, 2014, 5 pages.
Translation of Notice of Rejection for Japanese Patent Application No. 2012-508621, mailing date of Feb. 10, 2014, 5 pages.
European Search Report for European Patent Application No. 10770232.6, mailing dated of Oct. 4, 2013, 8 pages.
European Search Report for European Patent Application No. 10770230.0, mailing date of Oct. 4, 2013, 7 pages.

* cited by examiner

SIMULTANEOUS DIFFERENTIAL THERMAL ANALYSIS SYSTEM

RELATED APPLICATIONS

This application claims priority to Provisional Application No. 61/173,764, filed Apr. 29, 2009, which is incorporated by reference in its entirety. Concurrently filed application entitled "Simultaneous Differential Thermal Analysis System," U.S. patent application Ser. No. 12/766,971, listing Robert L. Danley and Xiaoping Hu as the inventors, is also incorporated in its entirety.

BACKGROUND

1. Field of the Invention

The present invention is related to apparatus for measuring thermal properties of samples of materials.

2. Background of the Invention

A simultaneous thermal or differential thermal analyzer (SDT) comprises a combination of a thermogravimetric analyzer, TGA (also known as a thermobalance), and either a differential thermal analyzer (DTA) or a differential scanning calorimeter (DSC). Thus, the instrument allows a user to simultaneously measure mass changes and to monitor a signal based on sensible or latent heat changes in the sample.

Thus, an SDT allows a user to measure both the heat flows (DSC or DTA) and weight changes (TGA) associated with transitions in a material as a function of temperature and time in a controlled atmosphere. Simultaneous measurement of these key material properties not only improves productivity but also simplifies interpretation of results. The complementary information obtained allows differentiation between endothermic and exothermic events which have no associated weight loss (e.g. melting and crystallization) and those which involve a weight loss (e.g. degradation). The combined evaluation also assures identical experimental and sampling conditions for both measurements, thereby eliminating those sources of uncertainty. Simultaneous DSC-TGA covers a wide temperature range from below ambient to above 1500° C., making it a powerful tool for studying a wide variety of materials including organic materials, notably polymers, and ceramics, metals, and other inorganic materials.

Typically, the design of such an SDT instrument comprises a combination of an existing microbalance component with a DTA or DSC measuring component. In fact, early SDT instruments were based on existing laboratory balances.

Generally, there are two types of microbalances in common use in SDT and TGA instruments, both of which employ the null balance principle, in which a restoring force is applied to the balance structure to maintain the balance in equilibrium. The restoring force, which is proportional to the change in weight, is the measured quantity in each type of microbalance. In both cases, the restoring force is applied electromagnetically as a response to a displacement of the balance structure, which is typically detected by optical means. Using such a balance, a very high degree of mass sensitivity and a very high resolution of changes in mass are readily obtained.

A first type of balance is the dual arm meter movement balance, in which a d'Arsonval meter movement (also referred to herein as a "meter movement balance") supports the balance beam and applies the restoring force as a torque.

In an SDT instrument that employs a d'Arsonval meter (also termed "meter movement"), when the sample weight in a sample holder connected to the balance changes during an experiment, a displacement sensor near the TGA balance senses movement of the balance away from the equilibrium position and electric circuitry generates the current necessary to restore the balance to equilibrium.

The second type of balance used in SDT and TGA instruments is the guided balance, in which the weighed mass is supported by a mechanism that constrains the movement of the weighed mass. Typically, the guided balance mechanism comprises a parallel four-bar linkage with elastic flexure pivots. This mechanism is termed a parallel guided balance. An electromagnetic actuator is used to apply a restoring force to the linkage, while a displacement sensor detects movement away from the equilibrium position and electric circuitry generates any current necessary to restore the balance to equilibrium.

SDT and TGA instruments may be classified as horizontal or vertical instruments based on the orientation of the heating furnace and the relative position of the balance. In principle, the measurement of weight may be perturbed by thermal expansion of the structure that extends into the furnace, and by forces exerted by movement of gas in the furnace caused by the action of purging the furnace or by buoyancy induced flows, in addition to buoyancy forces resulting from gas density changes. The magnitude of these weighing errors depends upon the configuration of the SDT instrument. In a horizontal furnace, thermal expansion of the beams that extend into the furnace may cause large weighing errors, while a vertical furnace configuration is largely immune to these effects, because thermal expansion occurs parallel to the Earth's gravitational field. On the other hand, vertical instruments are far more susceptible to fluid forces because thermal gradients in the furnace are parallel to the direction of the gravitational field which favors buoyancy driven flows and because the movement of the balance mechanism is parallel to the direction of purge gas flow. Horizontal instruments are largely immune to these forces because temperature gradients in the furnace are orthogonal to the gravitational field which is unfavorable to buoyancy driven flows and the movement of the balance mechanism is orthogonal to the direction of purge gas flow. Finally, buoyancy forces due to gas density changes may affect both horizontal and vertical furnace configurations to a similar degree.

As noted above, an SDT instrument combines a TGA measurement with a DTA or DSC type measurement, which requires that at least the sample side of the heat flow rate sensing device be supported by the balance mechanism. During sample measurement, a sample can be heated or cooled to examine changes in the sample induced by changes in temperature. In the case of sample heating, the heating takes place while at least a portion of the member supporting the sample extends into a furnace used to heat the sample. As the sample is heated, mass changes in the sample cause the balance mechanism to deflect from equilibrium, such that the restoring force needed to maintain the equilibrium can be measured. At the same time, a thermal signal (either DTA or DSC) is transmitted using wires that extend from the sample region to the stationary part of the instrument, so that analysis of the material changes taking place can be performed based upon the thermal signals received from the sample. Thus, the wires that carry the DSC or DTA signals from the sample region must connect the moving part of the balance to the fixed part. These signal wires typically exert a parasitic force on the balance that constitutes a weighing error.

Several factors can lead to the result wherein the wires contribute to weighing errors in SDT measurements. In principle, the forces exerted by the wires on the balance need not result in weighing errors, as long as the response in the wires to a displacement is linearly elastic. In other words, if the forces the wires exert are strictly linearly proportional to the displacement of the wires and the proportionality constant does not change, weighing errors caused by the wires could be avoided. If the response of the wires is not linearly elastic, weighing errors will result. Because the wires are usually deformed during installation in the SDT apparatus, the wires will almost always exert some force on the balance regardless of the balance position or whether any motion is taking place. No force would be exerted by the wires on the balance only if they were in their undeformed position. Another problem that may arise is that the wires may relax over time, resulting in changes in the force exerted by the wires. Typically, the wires are bent to the required shape when they are installed in the SDT apparatus, such that the deformation of the wires is at least partially plastic in nature. Over time, some of the plastic strain relaxes, thus changing the force exerted by the wire in a static position, as well as the force resulting from a displacement of the balance. In principle, the wires can be annealed or stress relieved, but given that they are generally fine and easily bent, it is difficult to handle and install the wires without deforming them.

In addition to wires, pivot structures that are necessary to connect fixed parts of a balance to moving parts of the balance, or that connect two moving parts of a balance, can introduce forces that may influence the measurement of sample weight.

Of the two types of balance, the meter movement type, given its lower mass and lower stiffness, is more sensitive and has faster dynamic response. The guided balance is more robust and is immune to the thermal expansion effects described above when used in a horizontal configuration. The guided balance-type SDT instrument may be used in conjunction with either the vertical or horizontal furnace configuration. Generally, the meter movement balance is used with the horizontal furnace configuration.

In the horizontal configuration, the meter movement balance is typically employed in a differential weighing configuration in which two balances, a sample and a reference balance, are operated in parallel. One balance weighs the sample and its container, while the other balance weighs an empty container or an inert reference sample in the container. Subtracting the reference weight measurement from the sample weight measurement eliminates the weighing error due to thermal expansion of the weighing structure and the weighing error due to buoyancy forces acting on the apparatus. Sample buoyancy forces are still a potential source of error in the dual balance configuration. Since the dual balance configuration employs a horizontal furnace configuration, the balances are largely isolated from forces arising from fluid motion, whether due to purge gas flow or to buoyancy differences resulting from temperature variations in the furnace, because these forces act orthogonally to the gravitational field.

In a dual balance meter movement type SDT (also termed "dual balance SDT" hereinafter) each of the sample and reference balances includes a meter movement component, optical displacement sensor and electronics to maintain the respective balance in the equilibrium position. Besides incurring undesirable cost because of duplication of components, a dual balance SDT system suffers from potential mismatches between the components of the two balance assemblies, such as in the meter movements. Another shortcoming of this design is that the meter movement components (or "meter movements") must support the entire weight of the balance beam and DTA or DSC sample holder structure.

D'Arsonval meter movements may be made with either jewel bearings or a thin taut band supporting the rotating part of the meter. Generally, taut band suspensions are preferred because they operate without friction. Displacement of the moving part of the meter twists the taut band slightly. Elastic deflection of the taut band is very linear and highly repeatable, whereas friction in jewel bearings is far more nonlinear and far less repeatable. On the other hand, jewel bearing meter movements can support much larger loads than those supported by taut band suspensions. Because a taut band suspension must support the entire weight of the beam, the sample (or reference) holder, DTA or DSC sensor, and sample, the weighing capacity is limited to a small fraction of the capacity of the taut band, most of which is used to support the beam, holder, and sensor. Thus, the taut band instruments tend to have low weighing capacity.

In view of the above, it will be appreciated that further improvement of balance apparatus in SOT instruments is needed.

SUMMARY OF THE INVENTION

In one aspect of the invention, an improved SDT configuration includes a horizontal meter movement balance structure that contains one or more members constructed from printed circuit board material (PCB). The PCB members are configured both to act as structural components of the balance and to conduct a signal from a sample or reference temperature sensor used in a DTA or DSC measurement.

In another aspect of the invention, an SDT balance comprises a plurality of PCB members that act as structural components and include conductors that run along the surface of the structural components and/or within the structural components so as to conduct electrical signals from sensor elements located in sample and reference holders. In one aspect of the invention, a continuous conductive path is formed that leads from a first PCB member to a second, adjacent PCB member, wherein the first and the second PCB member are mutually connected by a conductive flexure pivot.

In a further aspect of the invention, one or more pivots of the PCB-based SDT apparatus are configured using a thin planar strip flexure, and are constructed so that the thin planar strip flexures can carry the DTA or DSC signals between components of the balance structure. In other words, the thin planar strip flexures serve two separate functions: they provide 1) a conductive link between adjacent PCB members or between a PCB member and another structural member of the SDT apparatus, and 2) a pivoting means that allows the adjacent PCB members or PCB member and other structural member to pivot about one another.

In accordance with the present invention, a thin planar strip flexure comprises an electrically conductive flexible member and an abutment structure. The abutment structure comprises two abutments wherein a first abutment is configured to attach to one end of a flexible member and the second abutment is configured to attach to the other end of the flexible member.

In one embodiment of the invention, the thin planar strip flexures are soldered directly to conductive traces on the printed circuit board material. In this embodiment a continuous electrical path is formed via the flexure between conductors on a first PCB and conductors on an adjacent PCB. The continuous electrical path runs from the conductor on the first PCB through a first abutment affixed to the first PCB, through a thin planar strip flexure member attached in a first region to the first abutment, through a second abutment attached to the thin planar strip flexure member in a second region, and into a second conductor connected to the second abutment on an adjacent PCB.

In another embodiment of the invention, the thin planar strip flexure pivots are mechanically fastened to conductive traces on the printed circuit board material. In this embodiment a continuous electrical path via the flexure is formed between conductors on a first PCB and conductors on an adjacent PCB. The continuous electrical path runs from the conductor on the first PCB through a first abutment affixed to the first PCB, through a thin planar strip flexure member attached in a first region to the first abutment, through a second abutment attached to the thin planar strip flexure member in a second region, and into a second conductor affixed to the second abutment on an adjacent PCB.

For example, the abutment structure of a thin planar strip flexure in an SDT apparatus comprises a conductive sheet of material such as sheet metal, e.g., copper or other highly conductive metal. In one configuration of the invention, an abutment comprises a pair of flat rectangular sheets or blocks between which the thin planar flexible member is held. An abutment at each end of the thin planar strip flexure precisely defines the flexible part of the assembly and provides an electrically conductive surface to affix the flexure assembly to the balance structure.

In one embodiment of the invention, one or more pivots of the PCB-based SDT apparatus are configured using a crossed-flexure design, and are constructed so that the crossed flexures can carry the DTA or DSC signals between components of the balance structure. In other words, the crossed-flexures serve two separate functions: they provide 1) a conductive link between adjacent PCB members or between a PCB member and another structural member of the SDT apparatus, and 2) provide a pivoting means that allows the adjacent PCB members or PCB member and other structural member to pivot about one another.

In accordance with the present invention, a crossed-flexure pivot comprises a crossed pair of electrically conductive flexible members and an abutment structure. The abutment structure comprises two pairs of abutments wherein a first pair of abutments is configured to attach to respective first ends of the pair of flexible members and a second pair of abutments is configured to attach to respective second ends of the pair of flexible members such that the first flexible member crosses the second flexible member.

In one embodiment of the invention, the crossed-flexure pivots are soldered directly to conductive traces on the printed circuit board material. In this embodiment a continuous electrical path via the crossed-flexure pivot is formed between conductors on a first PCB and conductors on an adjacent PCB. The continuous electrical path runs from the conductor on the first PCB through a first abutment affixed to the first PCB, through a first crossed-flexure member attached in a first region to the first abutment, through a second abutment attached to the crossed-flexure member in a second region, and into a second conductor connected to the second abutment on an adjacent PCB.

In a preferred embodiment of the invention, the crossed-flexure pivots are mechanically fastened to conductive traces on the printed circuit board material. In this embodiment a continuous electrical path via the crossed-flexure pivot is formed between conductors on a first PCB and conductors on an adjacent PCB. The continuous electrical path runs from the conductor on the first PCB through a first abutment affixed to the first PCB, through a first crossed-flexure member attached in a first region to the first abutment, through a second abutment attached to the crossed-flexure member in a second region, and into a second conductor connected to the second abutment on an adjacent PCB.

In one variant of the present invention, the abutment structure of a crossed-flexure pivot in an SDT apparatus comprises a conductive sheet material such as sheet metal, e.g., copper or other highly conductive metal. In one configuration of the invention, an abutment comprises a generally L-shaped structure in which a first leg of the "L" is affixed to a surface of a structural member, such as a PCB, and a second leg of the "L" extends outwardly from the surface of the structural member. In one embodiment of the invention, the second leg of the "L" of an abutment is folded on itself so as to form a slot region that accommodates an end portion of a flat flexible member.

In accordance with an embodiment of the present invention, the pair of flat flexible members forms a substantially orthogonal cross when the SDT apparatus is in an equilibrium position for weighing. In one configuration of the invention, each flat flexible member comprises a thin planar conductive strip in which the plane of the strip is substantially orthogonal to the plane of the PCB member.

In accordance with an embodiment of the present invention, the abutments comprise a sheet metal material, such as copper, that is configured for easy soldering to conductive traces located on the PCB.

In accordance with embodiments of the present invention, an SDT instrument comprises a PCB/cross flexure pivot design in which adjacent structural members comprise two different PCB members or a PCB member and a non-PCB member that are electrically and mechanically coupled using a cross-flexure pivot. The SDT instrument comprises a horizontal meter movement balance.

In accordance with an embodiment of the present invention, to avoid extraneous thermoelectric voltages that could be generated where different materials are in contact, for instance where the flex pivots are soldered to the PCB material, the balance structure is housed in an enclosure that is maintained at constant uniform temperature. The beams used to support the sample holders attach to the balance structure within the constant temperature enclosure.

In accordance with embodiments of the present invention, in a meter movement balance SDT, the sample holders, including thermocouples for the DTA or DSC measurement, are made of high temperature resistant materials, such as high purity ceramics and platinum alloys.

In accordance with another configuration of the present invention, a single balance meter movement SDT instrument ("single meter movement SDT") comprises a single meter movement, single displacement sensor and single set of control electronics configured to replace a dual balance configuration, thus reducing complexity and eliminating weighing errors due to mismatch between different meter movements, displacement detectors and associated electronics.

In accordance with an embodiment of the present invention, the single meter movement SDT comprises two balance beam assemblies that are each connected to an end of an equal-arm meter movement balance. In accordance with an embodiment of the present invention, each balance beam assembly comprises a structure that includes a sample or a reference holder, a sensor for a DTA or DSC measurement, a balance beam member fabricated of printed circuit board material including conductors for the DTA or DSC sensor signals, and a flexure pivot assembly to support the balance beam assembly. The flexure pivot may comprise either a flat planar strip flexure pivot or a crossed-flexure pivot.

In accordance with an embodiment of the present invention, the single meter movement SDT is constructed in such a way that the majority of the weight of the weighing structures is supported by flexure pivots instead of by taut bands of the meter movement.

In another embodiment of the invention, the pivot point used in a single meter movement SDT is a flat planar strip flexure pivot. By appropriate placement of the pivot, the meter movement need only support the weight of the sample and sample and reference containers, increasing the weighing capacity of the balance. In other words, the flat planar strip flexure pivot assembly supports each balance beam assembly at a position that is very close to its center of gravity; thus, the flat planar strip flexure pivot supports the majority of the mass of the balance beam assembly, wherein the sample holder is accordingly disposed at one end of the beam assembly and the attachment to the equal arm meter movement balance is disposed at the opposite end of the beam assembly.

In another embodiment of the invention, the pivot point used in a single meter movement SDT is a crossed flexure pivot. By appropriate placement of the pivot, the meter movement need only support the weight of the sample and sample and reference containers, increasing the weighing capacity of the balance. In other words, the crossed flexure pivot assembly supports each balance beam at a position that is very close to its center of gravity; thus, the crossed-flexure pivot supports the majority of the mass of the balance beam assembly, wherein the sample holder is accordingly disposed at one end of the beam assembly and the attachment to the equal arm meter movement balance is disposed at the opposite end of the beam assembly.

In accordance with an embodiment of the present invention, a first and a second balance beam assembly of a single meter movement SDT are arranged in parallel, each being connected to a respective first and second arm of the equal-arm meter movement balance by a respective first and second flexible link. In this embodiment of the present invention, preferably, the majority of the weight of each balance beam assembly is carried by a pivot, such as a flat planar strip flexure pivot or a crossed-flexure pivot, placed near the center of gravity of the balance beam assemblies. Accordingly, the load carried by the single meter movement balance is reduced to just that imparted by the experimental sample, sample container, the reference material, if any, and the reference container.

In a preferred embodiment of the present invention, the pivot point of a single meter movement balance configuration is arranged such that the force that the balance beams exert on the arms of the meter movement counteracts the weight of the meter movement frame and coil, such that the taut band of the meter movement experiences little or none of the weight of the meter movement frame and coil.

In accordance with an embodiment of the present invention in which a balance beam member of the single meter movement SDT is made at least partly of a PCB material and supported by a flexure pivot, signals from the sample and reference DTA or DSC sensors are transmitted by conductors disposed on the PCB material part of the balance beam assembly through the flexure pivots to the stationary part of the SDT, eliminating the parasitic forces of wires that would otherwise be required for transmitting signals from the reference and sample holders. The advantages of cancellation of thermal expansion and fluid forces of a horizontal differential weighing assembly are preserved.

To avoid extraneous thermoelectric voltages that could be generated where different materials connect, for instance where the flex pivots are soldered to the PCB material, the balance structure is housed in an enclosure that is maintained at constant uniform temperature. The sample holders, including sensors for the DTA or DSC measurement, are made of high temperature resistant materials, typically high purity ceramics and platinum alloys. The beams attach to the balance structure within the constant temperature enclosure.

BRIEF DESCRIPTION OF THE DRAWINGS

FIG. 1a shows in perspective view a prior art configuration of a measurement apparatus portion of an SDT using a meter movement balance.

FIG. 1b shows a close up of a sample holder of the apparatus of FIG. 1a.

DETAILED DESCRIPTION

The present invention provides novel and inventive arrangements of components that can be used in apparatus that combine simultaneous gravimetric measurements of a sample with measurements of the sample that require propagation of electrical signals from the sample area to an apparatus for recording the electrical signals. For example, embodiments of the present invention provide improved configurations of sample measurement balances that can be used in conjunction with thermal measurements in an SDT apparatus.

As described above, SDT apparatus perform simultaneous gravimetric measurements together with thermal measurements, such as DSC or DTA. An SDT apparatus can simultaneously measure changes in a plurality of sample properties that take place during heating, such as changes in weight, phase changes, and the like.

Figure 1:
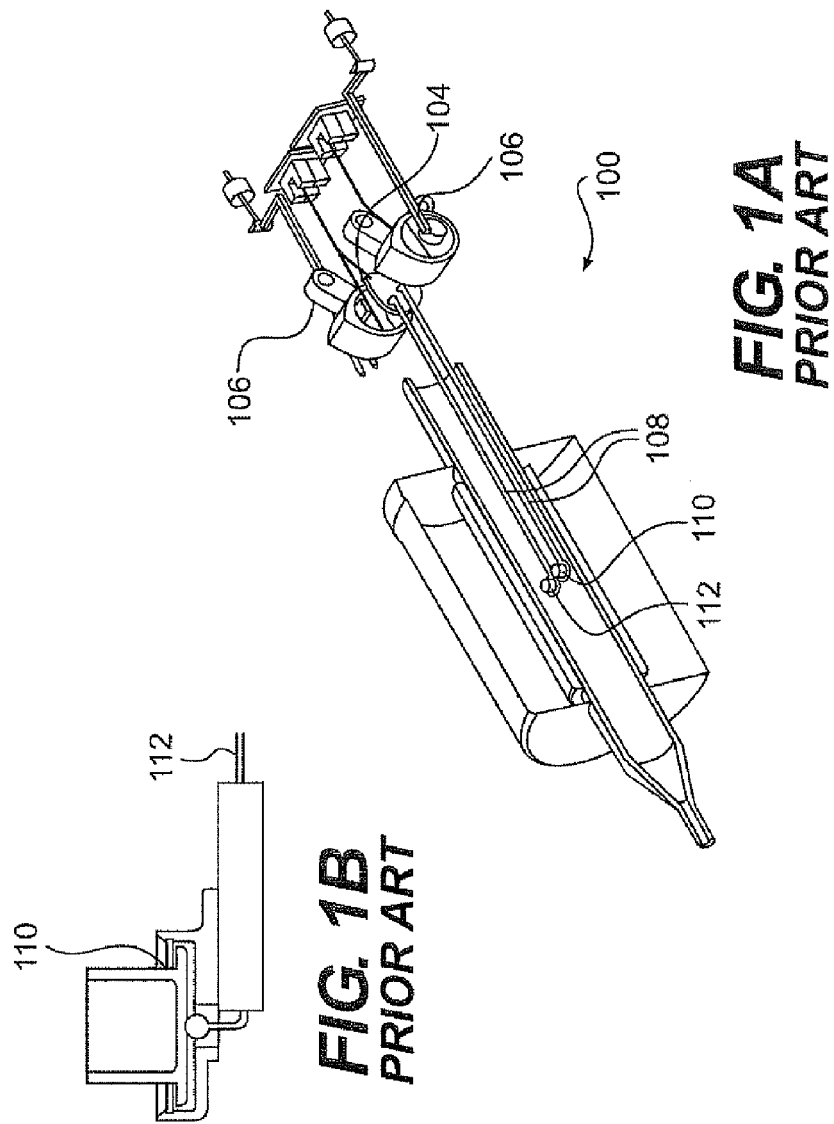

FIGS. 1a and 1b depict a known configuration of a measurement apparatus portion 100 of an SDT apparatus, in this case, a meter movement balance SDT. Apparatus 100 includes hardware for performing simultaneous thermal measurements (e.g., DSC or DTA) and gravimetric measurements of a sample placed in sample holder 112. The term "thermal measurements," as used herein, refers to measurements that are facilitated with the use of a thermocouple or similar device that is located at or near a sample or reference holder 110. The thermal measurements can be, for example, measurements for sensing heat flow rate, as in known DSC/DTA sensors. A hallmark of the thermal measurements is that an electrical signal propagates along conductors leading from the sample area and is detected and analyzed by components (not shown) that are external to measurement apparatus 100.

Apparatus 100 includes a differential horizontal balance that contains two meter movements 106 and accompanying sensors that are used to separately weigh samples and references placed in the sample and reference holders of respective sample and reference balance arms 108. Electrical signals are conducted from each thermocouple using wires that run from the sample or reference to an external point for detecting the electrical signals. In this apparatus, the electrical wires can exert a force on the balance arms that can interfere with accurate measurement of weight changes taking place in the sample. For example, a set of wires 104 coupled to the sample holder may exert a different force on the sample balance arm than that exerted on the reference balance arm by wires coupled to the reference holder. In this manner, the differential change in weight between the sample and reference material that may occur as the sample is heated can be obscured by the parasitic effect of the force exerted by wires, which may be unpredictable and of unknown magnitude. Similarly, in parallel guided balances, wires coupled to the sample and reference holders, for example, at pivot points of balance arms, can degrade the accuracy of weight measurements.

In accordance with the present invention, an improved balance assembly is provided that is compatible for use in SDT apparatus in which an electrical signal is conducted from a sample holder that is coupled to the balance. In an embodiment of the present invention, a balance assembly includes one or more composite structural members (also termed "composite members" herein, which refers to the fact that the members may have an insulating part and a conductive part) that include an insulating portion and conductive portions, for example, conductive paths that are configured to conduct electrical signals from a sample or reference sensor. The structural members thus perform a mechanical function and may also perform an electrical function. For example, the structural members can be fabricated from printed circuit board material (PCB) or similar material, or another type of insulator material, such as glass, glass ceramic, or other material. A conductive material is disposed on and/or within the insulator. The conductive material can be plated metal, deposited metal, or similar known conductors that are used in printed circuit boards, for example.

In an embodiment of the invention, the composite member is used as a horizontal member of an SDT balance, such as a horizontal member of a horizontal balance arm of a meter movement balance. In accordance with embodiments of the present invention, conductive paths disposed within and/or upon the surface of a composite member are used in place of wires to conduct electrical signals from sample and reference sensors.

In accordance with embodiments of the present invention, the composite members are configured to mechanically couple with the rest of a balance assembly so as to reduce any parasitic force acting on the balance in comparison to known SDT balances in which wires are used to transmit signals between adjacent components where a relative motion takes place between components. In one variant of the present invention, the mechanical coupling of a composite member to an adjacent member is facilitated using a pivot, such as a crossed-flexure pivot. The pivot is formed from a conductive material, such as a sheet metal and is configured to electrically couple conductive paths disposed on the composite member with conductors disposed in the adjacent component so as to form a continuous electrical path between the adjacent components that is not interrupted when the adjacent components are pivoted with respect to one another.

Figure 2:
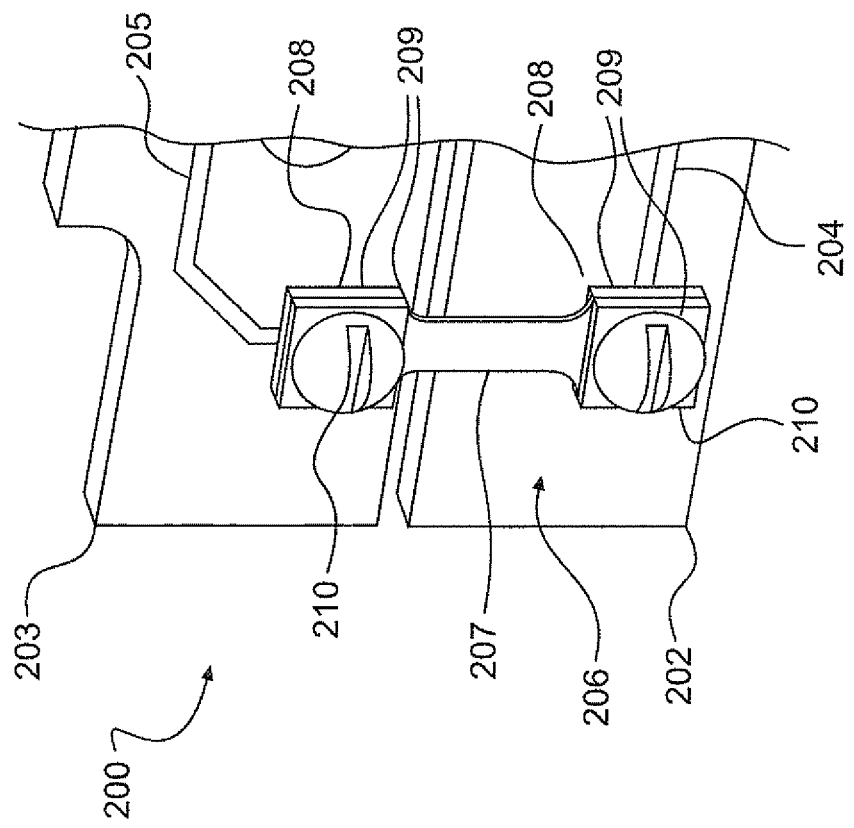
FIG. 2 depicts a portion of a balance having a thin planar strip flexure to couple adjacent structural members, in accordance with an embodiment of the present invention.

FIG. 2 depicts a coupling assembly 200 of a balance in which a thin planar strip flexure is configured to mechanically and electrically couple adjacent composite members, in accordance with an embodiment of the present invention. The adjacent composite members 202 and 203 can be, for example, an insulating substrate that is provided with conductive paths (also termed "traces" herein) on its surface and/or within the substrate. Specifically, the composite members 202 and 203 can be PCB material that is provided with conductive paths 204 and 205. The composite member can also be formed using conductive traces formed upon and/or within another insulator, such as a ceramic, glass ceramic, and glass, among other materials. In one variant of the invention, coupling assembly 200 is a pivot for a horizontal balance arm. In the embodiment of the invention depicted in FIG. 2, adjacent composite members 202 and 203 are substantially flat structures typical of PCBs. Flat planar strip flexure 206 comprises the flexure member 207 and the abutments 208. Flexure member 207 comprises a thin sheet of metal such as beryllium copper that has high electrical conductivity and high mechanical strength. For example, the beryllium copper alloy may be 1.8% to 2.0% beryllium. Typical dimensions of the strip are 0.001" thick by 0.065" wide by 0.200" long. Abutments 208 each comprise a pair of square copper plates 209 (oxygen-free copper preferred) that are considerably thicker than flexure member 207 and between which the flexure is mounted. In the present invention, screws 210 pass through holes in the abutments and the flexure to clamp them together and fix them to PCB structures 202 and 203. The abutments also contact conductive traces 204 and 205, thereby creating an electrically conductive path between the two traces via the abutment structures and the flexure member. Alternatively, the abutment structures could be soldered to the flexure and the assembly could be soldered to the conductive traces.

Figure 3:
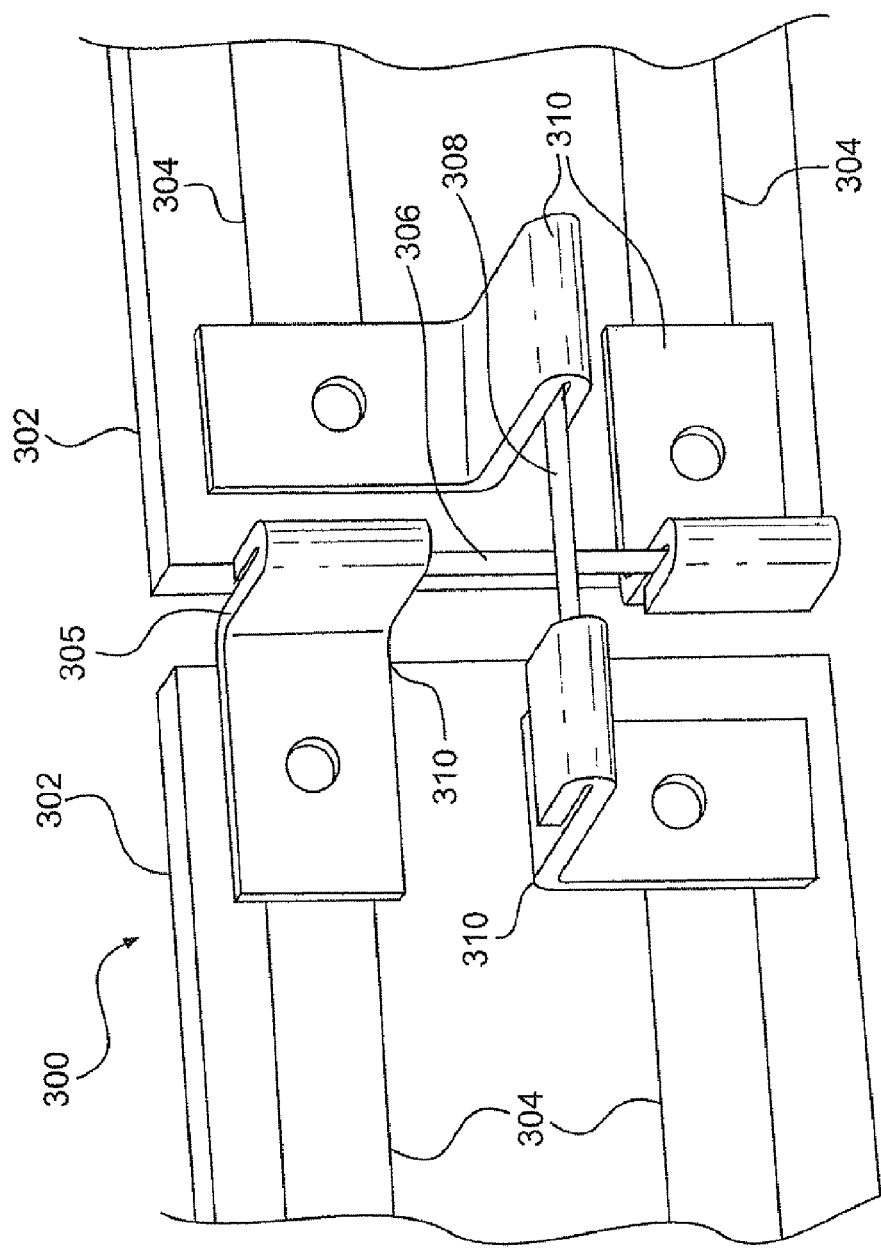
FIG. 3 depicts a portion of a balance having a crossed-flexure pivot to couple adjacent structural members, in accordance with an embodiment of the present invention.

FIG. 3 depicts a coupling assembly 300 of a balance in which a crossed-flexure pivot is configured to mechanically and electrically couple adjacent composite members, in accordance with an embodiment of the present invention. The adjacent composite members 302 can be, for example, an insulating substrate that is provided with conductive paths (also termed "traces" herein) on its surface and/or within the substrate. Specifically, the composite members 302 can be PCB material that is provided with conductive paths 304. The composite member can also be formed using conductive traces formed upon and/or within another insulator, such as a ceramic, glass ceramic, and glass, among other materials.

For example, coupling assembly 300 can be a pivot point for a horizontal balance arm. In the embodiment of the invention depicted in FIG. 3, adjacent composite members 302 are substantially flat structures typical of PCBs.

The adjacent composite members 302 each include two abutments 310 that, together with vertical flexure 306 and horizontal flexure 308, form a crossed-flexure pivot 305 that connects the adjacent composite members. In accordance with an embodiment of the present invention, abutments 310 are formed from a thin conductive material, such as sheet metal, for example, oxygen-free copper or another metal that can easily be electrically coupled to conductive paths 304. In one example, abutments 310 are soldered to conductive paths 304. In accordance with alternative embodiments of the invention, the conductive traces 304 that are coupled to abutments 310 can be additionally configured to conduct signals from a DTA or DSC sensor, or can be used solely for the purposes of affixing the abutments to the body of the composite member 302.

In the example shown in FIG. 3, abutments 310 have an "L" shape. However, abutments 310 can also assume other shapes. Crossed-flexures 306, 308 each are formed from thin conductive materials, such as sheet metal.

In accordance with embodiments of the present invention, coupling assembly 300 is configured to improve the performance of a measuring apparatus, such as an SDT apparatus. Composite members 302 are configured to provide sufficient mechanical rigidity and strength so as to act as structural members of a balance, as noted above. In addition, because the body of composite members 302 is electrically insulating, a plurality of conductive paths 304 that are electrically isolated from other paths can be formed on the composite members. Moreover, the cross-flexure pivot 305 provides a means for the mutually adjacent members 302 to pivot with respect to one another while simultaneously providing an electrically conductive connection between conductive paths on the adjacent composite members. This eliminates the need for electrically conductive wires to couple between the adjacent members. Accordingly, parasitic mechanical forces from wires that could act upon balance members are eliminated.

In the example shown in FIG. 3, adjacent composite members 302 are disposed substantially parallel to one another. In other embodiments of the present invention, a coupling assembly having a cross-flexure pivot could comprise adjacent composite members that are disposed at an angle to one another, for example, at a normal angle. In addition, one adjacent composite member can be a PCB board having electrical traces while the other adjacent composite member can be another insulator that supports conductive paths.

Figure 4:
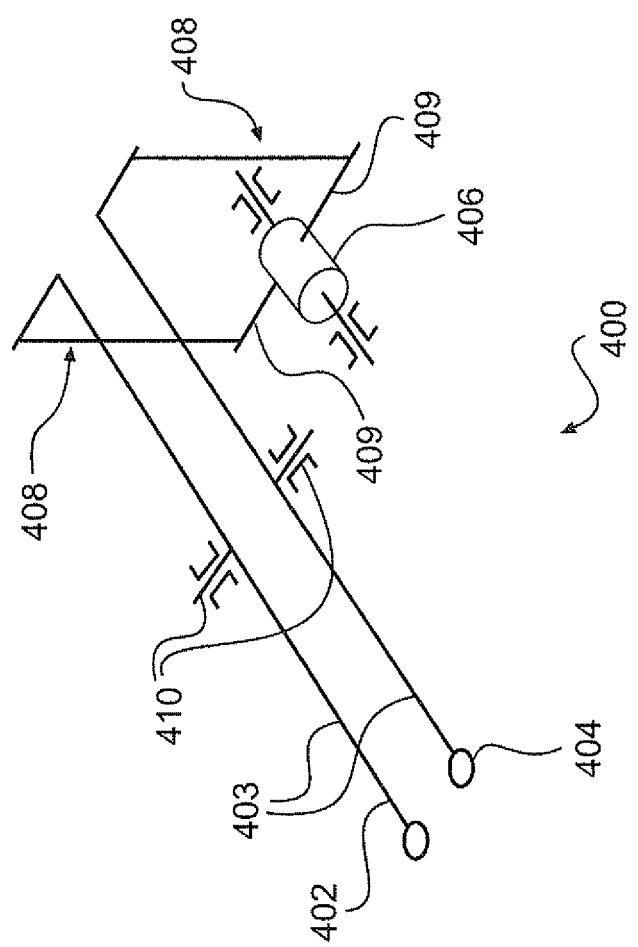
FIG. 4 depicts a perspective view of a schematic of a single meter movement balance and thermal measurement arms of an SDT apparatus, arranged in accordance with an embodiment of the present invention.

FIG. 4 depicts a schematic view of a single meter movement balance arrangement 400, in accordance with an embodiment of the present invention. Single meter movement balance arrangement 400 can be used, for example, in a TGA instrument, or in an SDT apparatus in which respective sample and reference holders 402 and 404 are coupled to balance beams 403 and are also connected to leads, such as thermocouple leads (not shown) for measuring temperature and heat flow rate to the sample and reference holders. Electrical signals that are conducted from holders 402 and 404 are conducted toward external devices configured, for example, for calculating, displaying, and or storing data related to heat flow. Single meter movement balance arrangement 400 provides a more simplified arrangement for measuring weight changes that take place in a sample when the sample is placed in a furnace (not shown). Although balance arrangement 400 includes two separate balance beams 403, one each for a reference 404 and a sample holder 402 (for simplicity, reference and sample holder arms are not shown as distinct from balance arms 403), the balance beams are each connected to the same single meter movement 406, which records the relative change in mass of a sample in sample holder 402. This is accomplished by coupling each balance beam 403 to a respective balance arm 409 of meter movement 406. As depicted, the balance beams 403 are coupled to the meter movement 406 through flexible links 408.

In accordance with the present invention, the single meter movement component 406 of balance arrangement 400 is configured similarly to known equal arm meter movements. In other words, the beam of meter movement 406 comprises a unitary structure that includes a center section to which two equal arm portions are fixedly attached. The center section of the beam is attached to the meter movement. The center section and equal arm portions rotate together when one side of the balance is heavier than the other. Thus, one balance arm 409 tends to rise and one balance arm tends to drop in response to a relative change in the weight experienced by the two balance beams 403. A displacement sensor (not shown) detects the motion and a current is generated in the meter coil (not shown) that creates a torque that restores the balance to the equilibrium position. The motor current is proportional to the extra weight on the heavier side of the balance. There is no calculation required other than the application of a proportionality constant to the generated meter current to determine a resultant mass, and a zero offset required to tare the balance. The single meter movement balance thus measures the weight difference between the balance arms directly. By contrast, in the known dual balance configuration, two separate weight measurements are performed and the difference between the two separate measurements is taken to compensate for buoyancy and thermal expansion effects of the balance apparatus.

The single meter movement arrangement depicted in FIG. 4 eliminates duplicate meter movements, sensors, and counterweights that exist in conventional dual meter movement balances (see FIG. 1a). In addition, because only a single meter movement and detector are used, weighing errors due to mismatches between different meter movements, and different detectors are eliminated.

In accordance with an embodiment of the present invention, each pivot 410 is placed at a position on a respective balance beam 403 that is very close to the balance beam center of gravity. Thus, pivots 410 support the majority of the mass of each balance beam, wherein the sample and reference holders 402 and 404 are accordingly disposed at one end of each balance beam assembly and the attachment to the equal arm meter movement balance 406 is disposed at the opposite end of the beam assembly.

Accordingly, the load carried by the single meter movement balance is reduced to just that imparted by the experimental sample, sample container, the reference material, if any, and the reference container. This increases the sample weighing capacity of a taut band meter movement in comparison to conventional arrangements in which the taut band must support the entire weight of the balance beam assembly.

For example, referring again to FIG. 1a, the balance arms 103 of conventional balance 100 are supported by and pivot around the taut band of the meter movements 106, thereby imparting the entire weight of the balance arms to the taut band.

In an embodiment of the present invention, the pivot point used in single meter movement arrangement 400 is a thin planar strip flexure.

In another embodiment of the present invention, the pivot point used in single meter movement arrangement 400 is a crossed flexure pivot.

In embodiments of the present invention, one or more portions of balance beam 403 can be made of composite members, such as a PCB material having electrically conductive paths formed on and/or within the PCB material, as described above. In a further embodiment of the present invention, balance beams 403 are constructed of a PCB material and pivots 410 are thin planar strip flexure that operate as described above. In yet a further embodiment of the present invention, balance beams 403 are constructed of a PCB material and pivots 410 are cross-flexure pivots that operate as described above.

When the force exerted upon a sample or reference pan changes, for example, when the mass of the sample in sample holder 402 or reference holder 404 changes, the force causes a movement in the respective balance beams 403, which movement exerts a force upon an arm 409 of meter movement 406 via flexible link 408. For example, if the sample in sample holder 402 becomes heavier the sample holder 402 and sample beam rotate downwardly about flexible link 408, which acts as a pivot, causing the back portion of the balance beam to rotate upwardly about the pivot formed by flexible link 408. The upward rotation induces an upward force on flexible link 408, which induces an upward force on left meter movement arm 409. This tends to rotate the meter movement arm, such that a displacement sensor detects the motion and generates a current in the meter coil that creates a torque that restores the balance to the equilibrium position. The change in meter current is proportional to the extra weight on the sample side of the balance. Thus, during sample heating or cooling, from a single reading of meter current, the difference in weight between sample and reference holders 402 and 404 can be determined. To the extent that the reference/reference holder/reference beam does not experience mass changes, this difference in weight between the two arms of the balance represents a change in mass of the sample in the sample holder 402.

In the case where both sample and reference holders/beams experience a simultaneous change in weight, meter movement 406 only registers the relative change in the sample weight between sample and reference holders. Thus, if a buoyancy force acts simultaneously on both holders, the sample and reference holders experience the same forces, which cancel each other out, such that no rotation of meter movement arms 409 takes place.

Accordingly, a TGA measurement can provide a direct measurement of the actual mass differences between the sample and reference holders, to the extent that changes in non-sample mass related forces that act on the balance and reference arms during an experiment, including buoyancy and apparatus thermal expansion, tend to act equally and in the same manner on both holders.

Figure 5:
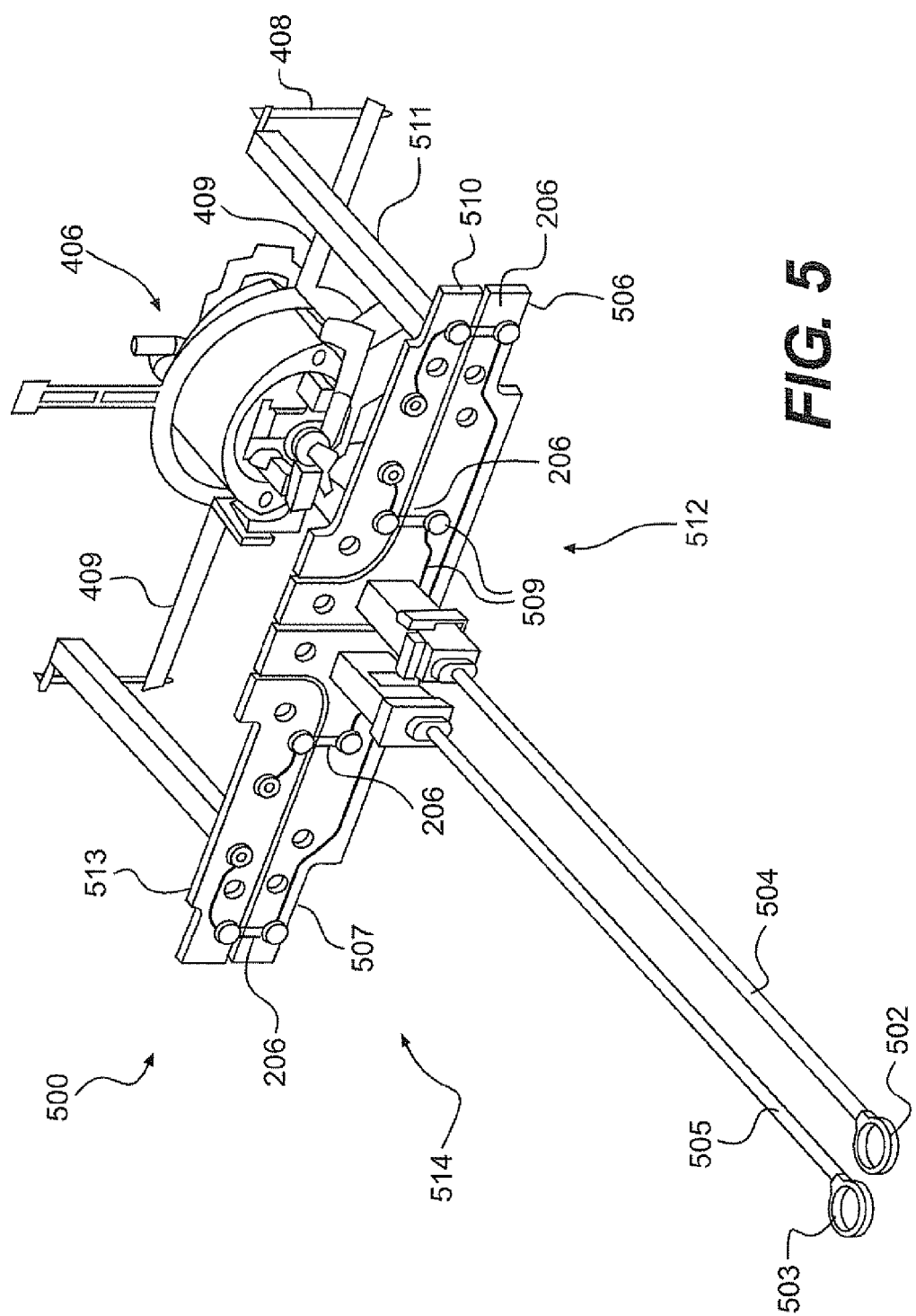
FIG. 5 depicts a perspective view of the single meter movement balance employing thin planar strip flexures in accordance with the present invention.

In accordance with an embodiment of the present invention, FIG. 5 depicts a perspective view of a twin-beam horizontal balance 500 having a single meter movement employing thin planar strip flexures, including sample and reference holders and beams of an SDT apparatus. The discussion above, in reference to the instrument shown in FIG. 4, with respect to the farce exerted on the sample and reference pans, applies equally to the instrument shown in FIG. 5, as well as to the instrument shown in FIGS. 6 and 7, described below.

Sample and reference holders 502 and 503 are joined to sample and reference beams 504 and 505 that are supported by sample and reference transverse members 506 and 507. Sample transverse member 506, made of PCB material is supported by one end of each of a pair of thin planar strip flexures 206 that are attached to conductive traces 509. The opposite end of each of the flexures is attached to the conductive traces of a stationary PCB member 510. Signal wires (not shown) from temperature sensors in sample holder 502 are connected to conductive traces 509 on transverse member 506. One end of rear beam 511 attaches to the opposite side of transverse member 506 from the sample beam 504. Sample holder 502, sample beam 504, transverse member 506 and rear beam 511 comprise the sample beam assembly 512. Thus, sample beam assembly 512 is supported by and pivots about thin planar strip flexures 206 and electrical signals from the sample sensor pass through the flexures, eliminating the need for signal wires connecting the moving sample beam to the stationary parts of the assembly.

The opposite end of rear beam 511 attaches to flexible link 408 which in turn attaches to arm 409 of meter movement 406. In a similar manner, reference sample holder 503 is attached to reference beam 505 and reference transverse member 507 which is supported by thin planar strip flexures 206 attached to stationary member 513. The signals from the temperature sensor in reference holder 503 are transmitted between the sensor and stationary member 513 in an analogous manner to that of the sample side. In all respects, the reference beam assembly 514 is identical to sample beam assembly 512 but is a mirror image.

Given that the electrical signal path from the temperature sensor passes through materials of differential composition from the connection point of the sensor wires to the stationary members, the possibility of generation of extraneous thermoelectric voltages exists. These thermoelectric voltages that would appear as a temperature measurement error on both the sample and reference temperature signals may be essentially eliminated by ensuring that the interconnection system is isothermal. The interconnection system includes: the ends of the signal wires, their connection to the conductive traces on the transverse member, the conductive traces on both the transverse members and the stationary members, the flexures including abutments and flexible members and the ends of the copper wires that connect to the conductive traces on the stationary members. The copper wires carry the sample and reference temperature signals to the measurement electronics. To ensure that the interconnection system is isothermal, thick plates (not shown) of high thermal conductivity material (typically copper or oxygen-free copper; silver or aluminum or other high thermal conductivity materials could also be used), surround and enclose the transverse members and their conductive traces, the stationary members and their conductive traces, the flexure assemblies and their attachments, the ends of the temperature sensor signal wires where they connect to the conductive traces on the transverse members and the ends of the copper signal wires where they connect to the conductive traces on the stationary members. Further, the isothermal plates and the interconnection system they enclose, rear beams, flexible links and meter movement assembly are housed within an enclosure whose temperature is precisely regulated at a temperature above ambient to ensure that everything within the enclosure remains at the constant temperature. This improves the temperature uniformity and stability of the isothermal plates and the temperature signal interconnect system they enclose, further ensuring that extraneous thermoelectric voltages do not create temperature errors in the sample and reference temperature sensor signals. In the case where the temperature sensors in the sample and reference holders are thermocouples, the reference junction temperature sensor necessary for applying reference junction compensation is installed in one of the isothermal plates, ensuring that the reference junction temperature sensor is at the same temperature as the plates and hence, the interconnection system.

Figure 6:
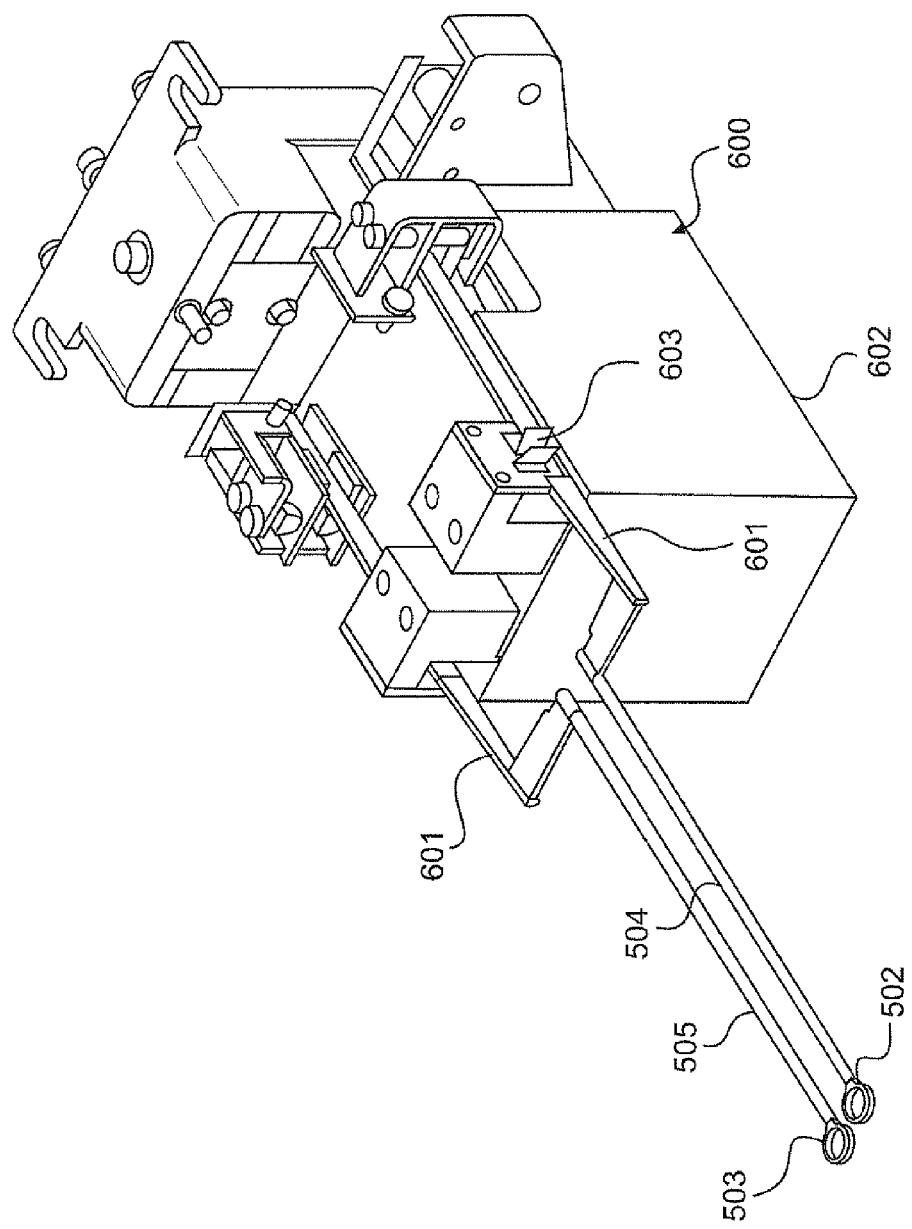
FIG. 6 depicts a perspective view of a single meter movement balance including thermal measurement arms of an SDT apparatus, arranged in accordance with an embodiment of the present invention.
Figure 7:
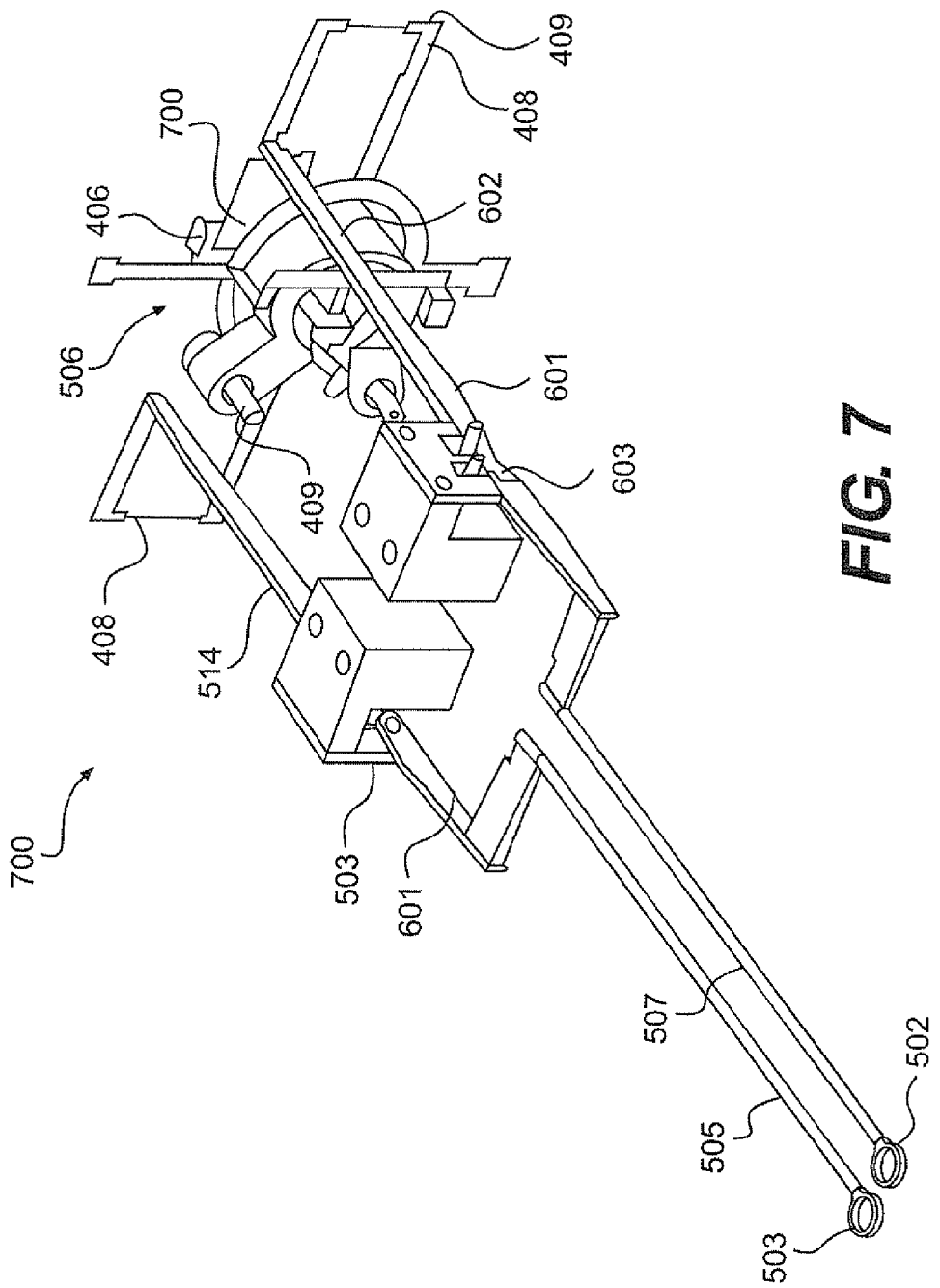
FIG. 7 depicts a perspective view of the apparatus of FIG. 6 with a housing portion removed.

Additionally, this ensures that the permanent magnet within the meter movement remains at constant temperature so that the magnetic field it creates remains constant. This is important because changes in the magnet temperature cause the field generated by the magnet to change, changing the proportionality of meter coil current to measured mass, thus introducing weight errors. The isothermal plates also act to protect the thin planar flexures from physical damage by excessive deflection of the sample and reference balance beam assemblies. The isothermal plates are made to fit very closely to the transverse members, thus limiting their movement such that if the balance assembly is deflected away from its equilibrium position, that motion is small enough that the elastic limit of the flexures will not be exceeded. Exceeding the elastic limit of the flexures would cause errors in the measured weight. In accordance with an embodiment of the present invention, FIGS. 6 and 7 depict a perspective view of a single meter movement balance 700 employing crossed-flexure pivots including sample and reference holder arms of an SDT apparatus, with a housing portion in place and removed, respectively.

Sample and reference holders 502 and 503 are connected to sample and reference beams 504 and 505, respectively. Sample and reference beams 504 and 505 are each connected to a respective sample or reference balance beam 601. Each balance beam 601 is configured to pivot about a pivot assembly 603 that is disposed on top of housing 602. A pivoting action induced in either sample or reference balance beam 601 exerts a force on a respective flexible link 408, which is connected to a respective meter movement arm 409. A frame structure of meter movement 406 comprises a unitary structure that attaches to the meter movement 406 near its axis, and two meter movement arms 409. The frame structure is configured to rotate about the axis of the meter movement, such that the two meter movement arms 409 rotate in unison. Accordingly, when one meter movement arm undergoes a rotational motion, the other meter movement arm undergoes a concomitant rotational motion in the same rotational direction.

The configuration of system 500 as depicted in FIG. 5 provides several additional inventive features. In contrast to the dual meter movement system of FIG. 1a, the rotation axis (and thereby, the pivoting) of balance arms 409 is orthogonal to the rotation axis of meter movement 406. Among other advantages, this results in the ability to place a pivot for balance beam assemblies 512 and 514 at any desirable point along the balance beams. Accordingly, the flexures 206 can be placed so as to exert an upward force on flexible link 408 that counteracts the weight of the frame of meter movement 406. This allows the balance shown in FIG. 5, as well as the balance shown in FIGS. 6 and 7, to minimize the static force applied to the taut band of meter movement 406 by the balance beam assemblies, thus increasing the weighing capacity of the assembly.

In accordance with an embodiment of the present invention, sample and reference holders 502 and 503 each includes a thermal sensor. The rate of heat flow in the sample and reference holders can be monitored from electrical signals received from the sensor according to one or more known techniques.

In accordance with an embodiment of the present invention, balance beams 512 and 514 comprise a composite material, such as a PCB material that provides conductive paths. For example, the transverse members 506 and 507 may be composite PCB/conductor as described above. Furthermore, one or more of pivots 206 can be a thin planar strip flexure whose structure and operation is described above with respect to FIG. 2. Accordingly, no wires are necessary to connect balance beam assemblies 512 and 514 to stationary parts of the balance assembly in order to conduct an electric signal to an external device.

In summary, embodiments of the present invention present novel and improved configurations for performing simultaneous thermogravimetric measurements of a sample and DSC or DTA type measurements, which require conducting electrical signals from sensors in the sample and reference holders. In accordance with embodiments of the present invention, composite members of a balance that serve both as mechanical members and as means to conduct electrical signals from the sample/reference holders are substituted for conventional balance members that serve only a mechanical function. A thin planar strip or a crossed-flexure pivot configuration is provided in conjunction with one or more composite members. These configurations serve to eliminate the need for wires at a junction between members that are movable with respect to one another. One or more aspects of the composite member/thin planar strip flexure or crossed-flexure pivot configurations can be incorporated into a twin beam horizontal single meter movement balance that is coupled, for example, through each of two equal arms, to a respective sample and reference balance beam assembly.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A coupling assembly for use in a balance, comprising:
a first composite member;
a second composite member coplanar with the first composite member; and
a pivot assembly configured to mechanically and electrically couple the first and second composite members, wherein the coupling assembly is configured to provide at least one continuous electrically conductive path that extends along at least a portion of the first composite member, between the first and second composite members, and along at least a portion of the second composite member;
wherein the first and second composite members are parts of a horizontal balance beam of a meter movement balance.

2. The coupling assembly of claim 1, wherein the balance is part of a simultaneous differential thermal analysis apparatus.

3. The coupling assembly of claim 1, wherein one or more of the first and second composite members is a printed circuit board material comprising conductive paths.

4. The coupling assembly of claim 1, wherein the pivot assembly comprises thin planar electrically conductive flexures.

5. The coupling assembly of claim 1, wherein the pivot assembly is a crossed-flexure pivot comprising a first crossed flexure member attached to the first composite member and a second crossed flexure member attached to the second composite member.

6. An instrument, comprising:
a holder assembly that includes sample and reference sensors that are configured for one of DSC and DTA measurements;
a first sample balance member mechanically coupled to the sample sensor of the holder assembly;
a second sample balance member pivotally connected to the first sample balance member using a pivot assembly;
a first reference balance member mechanically coupled to the reference sensor of the holder assembly;
a second reference balance member pivotally connected to the first reference balance member using a pivot assembly;
wherein each of the balance members is a composite member that includes electrically conductive paths that are affixed to an insulating portion of the composite member, wherein the instrument is configured to conduct electrical signals along an electrically conductive path that extends from the sample and/or reference holder assembly along at least a portion of the respective first balance member, through the pivot assembly and along at least a portion of the respective second balance member.

7. The instrument of claim 6, wherein at least one of the balance members comprises a printed circuit board material that includes conductive metal traces.

8. The instrument of claim 6, wherein the balance members each comprise a substantially flat planar surface, and wherein an angle between surfaces of planes that define the balance member is one of about zero degrees and about ninety degrees.

9. A balance for use in a simultaneous differential thermal analysis instrument, comprising:
   a sample balance beam rigidly coupled to a sample holder;
   a reference balance beam rigidly coupled to a reference holder; and
   a meter movement mechanically coupled to each of the sample and reference balance beams, wherein the meter movement comprises a taut band d'Arsonval meter movement, and
   wherein a first meter movement arm of the meter movement is mechanically coupled to the sample balance beam by a first flexible link and a second meter movement arm of the meter movement is mechanically coupled to the reference balance beam by a second flexible link.

10. An instrument comprising:
   a sample balance beam rigidly coupled to a sample holder;
   a reference balance beam rigidly coupled to a reference holder; and
   a meter movement mechanically coupled to each of the sample and reference balance beams, wherein the meter movement comprises a taut band d'Arsonval meter movement, a first meter movement arm and a second meter movement arm,
   wherein the sample balance beam comprises:
      a first member that is rigidly coupled to the sample holder; and
      a second member that is pivotally coupled to the first member through a first pivot and the first member is flexibly coupled to the first meter movement arm through a first flexible link, and
   wherein the reference balance beam comprises:
      a first member that is rigidly coupled to the reference holder; and
      a second member that is pivotally coupled to the first member through a second pivot and the first member is flexibly coupled to the second meter movement arm through a second flexible link.

11. The instrument of claim 10, wherein the first and second members of each of the sample and reference balance beams comprise a printed circuit board material, and wherein the first and second pivots are crossed-flexure pivots.

12. The instrument of claim 10, wherein the first and second members of each of the sample and reference balance beams comprise a printed circuit board material, and wherein the first and second pivots are planar flexure pivots.

13. The instrument of claim 10, wherein the first and second pivots are configured to support the respective sample and reference balance beams at first and second positions that are very dose to a center of gravity of the respective sample and reference balance beams.

14. The instrument of claim 10, wherein the first meter movement arm and the second meter movement arm extend in a substantially horizontal direction.

15. A simultaneous differential thermal analysis instrument, comprising:
   a holder assembly that includes a means for conducting electrical signals from the holder assembly, the holder assembly including a sample holder and a reference holder;
   a first composite balance member mechanically coupled to the sample holder;
   a second composite balance member mechanically coupled to the reference holder;
   a stationary member; and
   a coupling means,
   wherein the coupling means comprises:
      pivot means for pivotally connecting the first and second composite balance members to the stationary member, and
      a means for providing a continuous electrically conductive path between conductive means on each of the first and second composite balance member and conductive means on the stationary member.

16. The simultaneous differential thermal analysis instrument of claim 15, wherein at least one of the first composite balance member, the second composite balance member, and the stationary member comprises a printed circuit board material.

17. The simultaneous differential thermal analysis instrument of claim 15, wherein the pivot means is a crossed-flexure pivot.

18. The simultaneous differential thermal analysis instrument of claim 15, wherein the pivot means is a planar flexure pivot.

19. A simultaneous differential thermal analysis instrument comprising:
   a sample balance beam having a sample holder attached at one end;
   a reference balance beam having a reference holder attached at one end, the reference balance beam being positioned parallel to the sample balance beam such that the reference holder is adjacent to the sample holder;
   a meter movement connected to the sample balance beam and to the reference balance beam adapted to measure the differential weight of the sample holder with respect to the weight of the reference holder, said weight of the sample holder including the weight of a sample in the sample holder, and said weight of the reference holder including the weight of any reference in the reference holder;
   temperature sensors on the sample holder and on the reference holder electrically connected to thin planar strip flexures mounted on a non-stationary sample transverse member and a non-stationary reference transverse member, respectively;
   conductive material forming a continuous electrical path electrically connecting the temperature sensors to the thin planar strip flexures,
   wherein the thin planar strip flexures electrically connect the conductive materials on the non-stationary sample and reference transverse members to conductive materials on stationary transverse members, which in turn are connected to apparatus for measuring the differential heat flow to the sample holder with respect to the reference holder.

20. The simultaneous differential thermal analysis instrument of claim 19, wherein the non-stationary sample transverse member and a non-stationary reference transverse member are constructed from printed circuit board material.

21. The simultaneous differential thermal analysis instrument of claim 19, wherein the thin planar strip flexures form pivots that allow the transverse members to move with respect to the stationary transverse members.

22. The simultaneous differential thermal analysis instrument of claim 19, wherein the thin planar strip flexures comprise abutments that attach the strip flexures to the transverse members.

23. The simultaneous differential thermal analysis instrument of claim 19, wherein
the non-stationary sample transverse member and a non-stationary reference transverse member are constructed from an insulator material, and the conductive paths are formed by plating or depositing or forming thin layers of the conductive materials on the insulator material.

24. A simultaneous differential thermal analysis instrument comprising:
a sample balance beam having a sample holder attached at one end;
a reference balance beam having a reference holder attached at one end, the reference balance beam being positioned parallel to the sample balance beam such that the reference holder is adjacent to the sample holder;
a meter movement connected to the sample balance beam and to the reference balance beam adapted to measure the differential weight of the sample holder with respect to the weight of the reference holder, said weight of the sample holder including the weight of a sample in the sample holder, and said weight of the reference holder including the weight of any reference in the reference holder;
temperature sensors on the sample holder and on the reference holder electrically connected to crossed-flexure pivots mounted on a non-stationary sample transverse member and a non-stationary reference transverse member, respectively;
conductive material forming a continuous electrical path electrically connecting the temperature sensors to the crossed-flexure pivots;
wherein the crossed-flexures electrically connect the conductive materials on the non-stationary sample and reference transverse members to conductive materials on stationary transverse members, which in turn are connected to apparatus for measuring the differential heat flow to the sample holder with respect to the reference holder.

25. The simultaneous differential thermal analysis instrument of claim 24, wherein the non-stationary sample transverse member and a non-stationary reference transverse member are constructed from printed circuit board material.

26. The simultaneous differential thermal analysis instrument of claim 24, wherein the crossed-flexure pivots allow the transverse members to move with respect to the stationary transverse members.

27. The simultaneous differential thermal analysis instrument of claim 24, wherein the crossed-flexures comprise abutments that attach the crossed-flexures to the transverse members.

28. The simultaneous differential thermal analysis instrument of claim 24, wherein the non-stationary sample transverse member and a non-stationary reference transverse member are constructed from an insulator material, and the conductive paths are formed by plating or depositing or forming thin layers of the conductive materials on the insulator material.

\* \* \* \* \*